United States Patent [19]

Anapliotis et al.

[11] Patent Number: 4,676,797
[45] Date of Patent: Jun. 30, 1987

[54] UNIT FOR RESECTION PROSTHESIS

[75] Inventors: Emmanuel Anapliotis; Curt Kranz, both of Berlin, Fed. Rep. of Germany

[73] Assignee: MECRON medizinische Produkte GmbH, Berlin, Fed. Rep. of Germany

[21] Appl. No.: 721,674

[22] Filed: Nov. 7, 1984

[30] Foreign Application Priority Data

Nov. 8, 1983 [DE] Fed. Rep. of Germany ....... 3340767

[51] Int. Cl.⁴ ................................................ A61F 2/30
[52] U.S. Cl. ......................................... 623/18; 623/23
[58] Field of Search ...................... 623/16, 17, 18, 19, 623/20, 21, 22, 23; 128/92 C, 92 CA; 403/334, 361, 13, 14

[56] References Cited

U.S. PATENT DOCUMENTS

| 1,393,930 | 10/1921 | Wolfe | 403/334 |
| 2,869,907 | 1/1959 | Deliso | 403/361 |
| 3,485,520 | 12/1969 | Alexander | 403/334 |
| 4,368,789 | 1/1983 | Orr et al. | 403/361 |

FOREIGN PATENT DOCUMENTS

| 11665 | 11/1978 | European Pat. Off. | |
| 3205577 | 10/1982 | Fed. Rep. of Germany | |
| 2475891 | 8/1981 | France | 623/22 |
| 2094629 | 9/1982 | United Kingdom | 623/22 |
| 0797680 | 1/1981 | U.S.S.R. | 623/22 |

Primary Examiner—Richard J. Apley
Assistant Examiner—David J. Isabella
Attorney, Agent, or Firm—Spencer & Frank

[57] ABSTRACT

A resection prosthesis assembly unit including a head member, an end member and an intermediate member between the head and end members, of which one member is provided with a conical pin and another member is provided with a conical bore, with the latter two members being provided with respective first surfaces which extend transversely to an insertion direction and which face one another and are spaced apart to define a recess when the two members are connected together, one of the two members being further provided with a second surface extending in the insertion direction, and the recess being provided to receive a wedge insertable into the recess to bear against the first surfaces for forcing the two members apart while the forces exerted by the wedge are absorbed by the first surfaces and the wedge is guided by the second surface.

11 Claims, 12 Drawing Figures

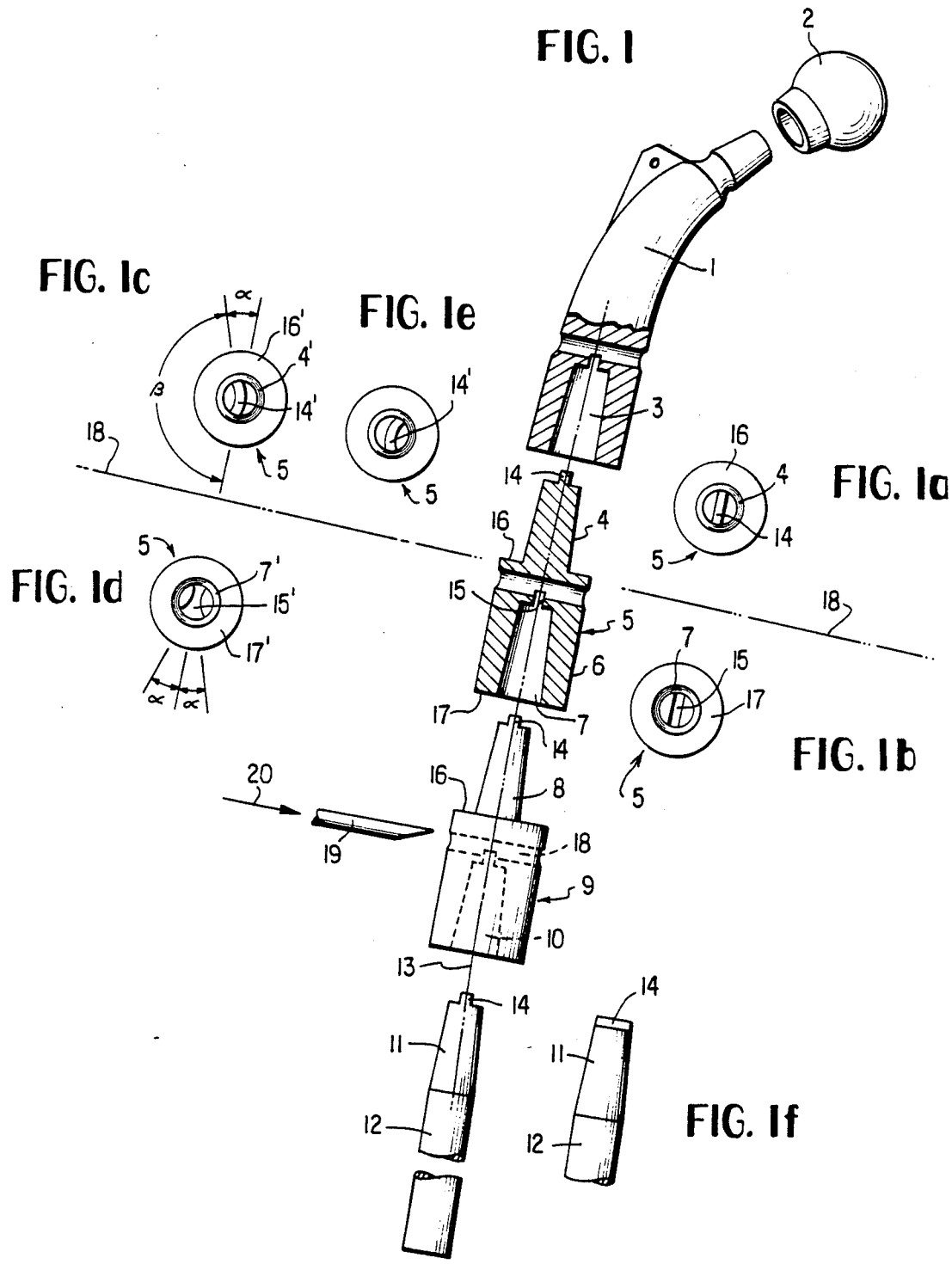

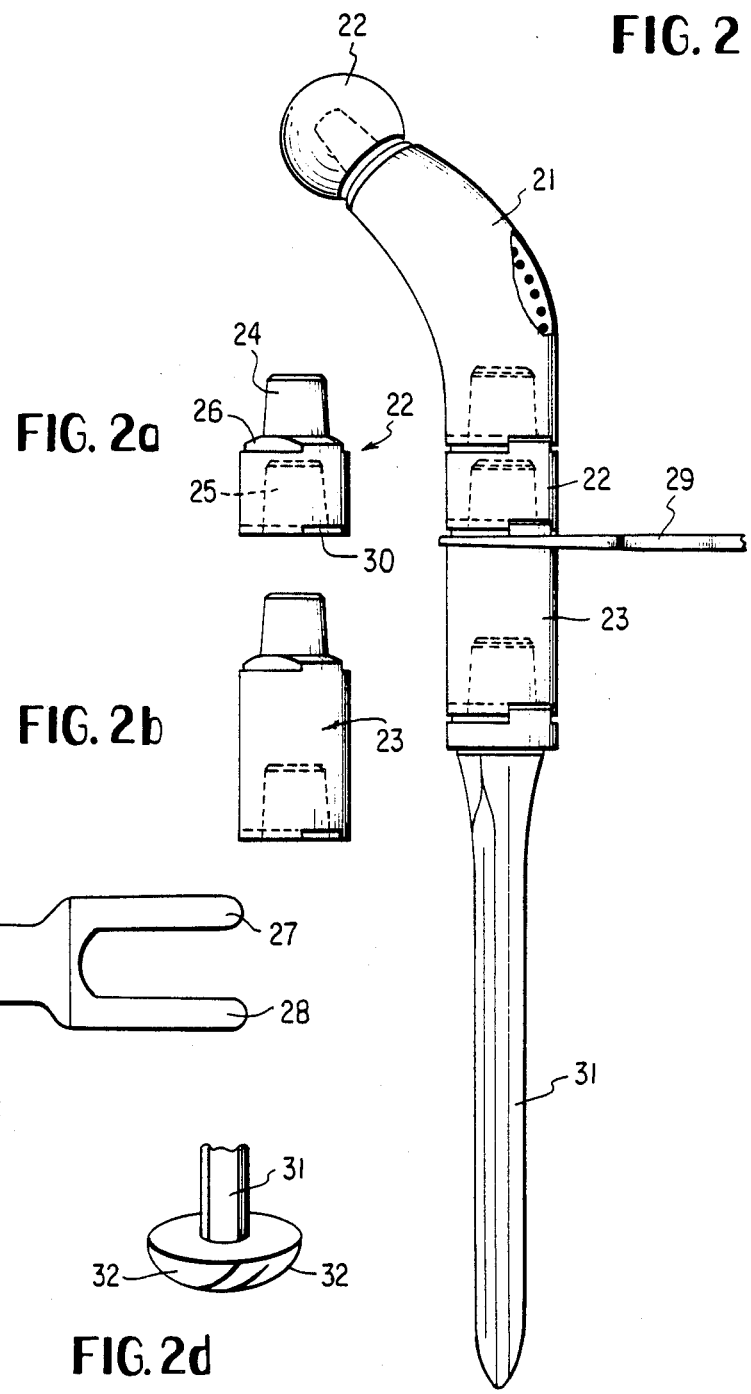

UNIT FOR RESECTION PROSTHESIS

BACKGROUND OF THE INVENTION

The invention relates to an assembly unit of the type composed of head and end members connected together via an intermediate member.

Such an assembly unit is disclosed in DE-OS No. 3,205,577. That pulication describes parts which can be assembled to form a femur prosthesis of any desired length and, when assembled, result in a relatively rigid, straight femur substitute. Their drawback is that disassembly, which may become necessary in the case of renewed surgery, is possible only with difficulty.

The drawback connected with the prior art prosthesis, that the individual parts are difficult to disassemble at a later date, produces difficulties particularly during renewed surgery and a change in the prosthesis necessitated in connection therewith. In such a case, it is desirable to be able to disassemble the parts of the prosthesis by simple manipulations so as to permit reassembly in a different manner, possibly with the use of different parts.

SUMMARY OF THE INVENTION

It is therefore the object of the invention as defined to provide a prosthesis assembly unit of the above-mentioned type which makes it possible to reseparate the parts of the prosthesis from one another without the expenditure of special forces and with the use of a simple tool.

In the invention it is of particular advantage that, when the parts are disassembled, the prosthesis need not be rotated for screw movements or the like so that disassembly of individual parts can take place even with the prosthesis shaft still partially implanted.

In preferred modifications of the invention, the wedge provided for the separation is given a fork shape so that the necessary force can engage in the edge regions of the prosthesis parts and no apertures are required which lead into its interior and which, due to the penetration of body fluids, could make release of the prosthesis parts from one another more difficult. At the same time, this also facilitates guidance and the rear region of the wedge can be made broader so that it can easily be struck by an appropriate striking tool even under difficult conditions.

Another advantage of the invention is that, with the wedge designed in the manner of a fork, recesses incorporating the faces in which interaction with the wedge results in the separation of adjacent elements can be made in the outer profile in such a way that they are hardly noticeable at all and, primarily, do not interfere with the functional capability of the prosthesis. If the recesses are formed by way of chamfers and the adjacent member is shaped accordingly, such chamfers can be gripped in such a way that security against rotation is provided simultaneously.

One advantageous modification of the present invention serves the purpose of providing an assembly unit for a resection prosthesis, particularly as femur substitute, which, in the assembled state, exhibits a shape that approximates the curvature of the natural thigh bone and thus also the corresponding physiological behavior under static and dynamic loads. As many parts as possible of the assembly unit are intended to be used for the left femur as well as for the right femur so as to simplify warehousing.

This further object is realized in that the longitudinal axis of the intermediate member is curved similarly to the femur and the shaped portions [thereon] are of such configuration that they fit into one another in two positions in which the abutting members are rotated about their longitudinal axes by an angle of 180° or an angle which comes close to the natural angle existing between the local planes of curvature of the longitudinal axes of the femur.

Other advantageous modifications of the invention are defined in the remaining dependent claims.

BRIEF DESCRIPTION OF THE DRAWING

The principle of the invention and of its embodiments will be explained in greater detail with the aid of emodiments that are illustrated in the drawings. It is shown in:

FIG. 1, an embodiment of a first assembly unit, including the head member supporting the joint ball;

FIGS. 1a through 1f, details of the assembly unit according to FIG. 1;

FIG. 2, a further embodiment of an assembly unit corresponding to FIG. 1; and

FIGS. 2a through 2d, details of the assembly unit according to FIG. 2.

DESCRIPTION OF THE PREFERRED EMBODIMENTS

In FIG. 1, a plug-in joint ball 2 is provided for head member 1 of a femur prosthesis. At its lower end, head member 1 is provided with a conical bore 3 into which the pin 4 of an intermediate member 5 comprising a circularly cylindrical body 6 and a conical bore 7 can be inserted.

The pin 8 of a further intermediate member 9 fits into conical bore 7. Intermediate member 9 is constructed essentially similarly to intermediate member 5 but has a different length. A plurality of such intermediate members 5, 9 can be assembled to form a shaft corresponding to the resection prosthesis shown in FIG. 1. The conical pin 11 of an end piece 12 can be plugged into the lower end of the shaft—namely, into the corresponding conical bore 10 of the last intermediate member 9. End piece 12 is provided with a conical pin and a cylindrical shaft which has a diameter less than that of the intermediate member and is intended to be cemented into the marrow cavity.

The longitudinal axis 13 of the illustrated resection prosthesis is slightly curved, similarly to the natural curve of the femur. Preferably, this curvature is concentrated in the region of intermediate members 5, 9, while head member 1 and end piece 12 are essentially straight in the shaft region. The slight curvature additionally provides a certain elasticity which better corresponds to the physiological elasticity. Moreover, this improves the introduction of force into the femur.

For the sake of simplifying the illustration, let it be assumed that the plane of curvature of longitudinal axis 13 lies in the plane of the drawing. In longer prostheses, the plane of the curvature may certainly differ locally—for example in a plane corresponding to the plane of the drawing in the higher disposed intermediate pieces. In other embodiments, the plane of the curvature may be inclined more or less with respect to the plane of the drawing or may be oriented in different directions in different height sections.

Since the effect of the slight curvature—which amounts to about 3 to 4 radians over the entire length of the prosthesis—on the individual parts can often be detected at these parts only with difficulty, it must be assured that these intermediate members are assembled correctly in such a manner that the desired total curvature results. To also provide assurance with respect to the correct direction of the curvature of the shaft in the neck region, matching (plug-in) shaped portions are provided as security against rotation about axis 13; these are provided in the form of tongues 14 at pins 4, 8 and 11 and grooves 15 in bores 3, 7 and 10. With the prosthesis assembled, the tongues and grooves mate.

To facilitate assembly, these shaped portions have only little play with respect to one another. Instead of tongues and grooves as the shaped portions, two lips may also be provided together with associated recesses or the like. These shaped portions may be provided at the ends of the pins and at the bottom of the bores as well as at abutting faces 16 and 17, respectively.

With respect to FIG. 1, the detail view of FIG. 1a is a top view of intermediate member 5, and particularly of the end of pin 4 which is provided with tongue 14. FIG. 1b is a top view of the other side of intermediate member 5 with face 17 of conical bore 7 and groove 15. If the drawing is folded about axis 18, it can be seen that pin 14 according to FIG. 1a fits into groove 15 according to FIG. 1b. It can also be seen that pin 14 fits into the groove even if intermediate member 5 of FIG. 1a is rotated by 180° about its longitudinal axis. Consequently, the curved intermediate members 5, 9 are not only suitable for assembling a left femur prosthesis but can also be used in a corresponding manner to assemble a prosthesis for the right side. The prerequisite is here that, with respect to the plane of the curvature for a prosthesis for the left side, the plane of curvature of the prosthesis for the right side must be pivoted by 180° about the center axis of the body.

However, this simplifying prerequisite is not true over the entire length of a thigh bone. Rather, there are regions in the femur where an angle beta of less than 180° lies between the plane of curvature on the left side and the plane of curvature on the right side. Suitable embodiments for this purpose are shown in FIGS. 1c and 1d (similar to FIGS. 1a and 1b). The reference numerals corresponding to FIGS. 1a and 1b are here provided with a prime. FIG. 1c indicates that tongue 14' is bent at the obtuse angle "beta". The angle constituting the difference between 180° and "beta" is marked "alpha". Groove 15 in FIG. 1d is widened in the manner of a wedge by twice the amount of this angle.

If the drawing is again imagined to be folded about line 18, it can be seen that tongue 14' fits into groove 15'. It can also be seen that, after rotation of intermediate member 5 (based on FIG. 1c) about the angle "beta", the position of FIG. 1e is obtained and tongue 14', now in its new position shown in FIG. 1e, likewise fits into groove 15' of FIG. 1d.

FIG. 1 further shows a way for loosening the conical connections. For this purpose, a bore 18 in intermediate member 9 takes care that, after insertion of end piece 12, a space remains between its tongue 14 and intermediate member 9 (more precisely: the upper wall portion of bore 18). This space is externally accessible through bore 18 for a wedge 19 which can be driven in in the direction of arrow 20 to press conical pin 11 back out of bore 10. Wedge 19 is here supported on tongue 14 so that, during the separation of members 9 and 12, the cone faces are protected.

Not shown in the drawing is a case for practical use in which the prosthesis parts are provided with a longitudinal channel for an anchoring rod which extends from head member 1 to end piece 12. This may be a thin throughgoing screw or preferably a flexible threaded rod which holds together the individual parts of the prosthesis. If a threaded rod is used, the latter may be shortened to the required length by means of a cutting tool, for example pliers. Such an anchoring rod is not obligatory since the conical connections seat themselves under load; however, it is useful as well for manipulation during surgery and for fixing the parts before the onset of the actual load from the patient's body weight.

FIGS. 2 and 2c show a further embodiment of the resection prosthesis according to the invention. A curved shaft member 21 receives the joint head 22 via a cone, with the cone being shown in dashed lines in this perspective illustration—corresponding to the connections to be made later.

Following the curved shaft member 21, there are two components of different lengths 22 and 23 which are shown separately once more in FIGS. 2a and 2b, respectively. By varying the length of the components, different prosthesis lengths can be realized. In element 22 shown in FIG. 2a, a cone 24 can be seen whose dimensions are adapted to the corresponding conical recess 25 shown in dashed lines with dimensions that are used uniformly in the entire system. At its side facing cone 24, element 22 is provided with two planar chamfers of which only chamfer 26, which is in front in the drawing, is visible. The two chamfers are parallel to one another and correspond in their spacing to the spacing between the interior faces of the two wedge-shaped tines 27 and 28 of a fork 29.

This fork 29 is driven between the elements from the side, as shown in FIG. 2. The fork-shaped wedge 29 can thus be inserted with ease and is guided without twisting by the two chamfers. Penetration of body fluids into interior regions of the prosthesis is impossible so that the prosthesis parts can later be easily released from one another. The wedge-shaped faces of part 29 here act on the lower delimitations of the chamfers and on the lower edge of the next higher member.

The lower region of the parts provided with a conical recess is provided with an additional recess 30 of such shape that the parts remaining next to the recess enclose, in the region of chamfers 26, the individual parts of the prosthesis at its side provided with cone 24 and thus secure it against rotation.

If it is desired to provide a shaft curvature corresponding to a prosthesis for the left or right side, the faces of the chamfer and of the recesses enclosing this chamfer should be designed according to the embodiment shown in FIGS. 1c through 1e.

In another embodiment—which is not shown in the drawing—the end region of shaft 31 is designed in such a manner that its lower region forms a receptacle for an artificial knee joint or it itself is shaped in such a manner that the necessary roll faces are provided at that part. Such a design of a total prosthesis results in high stability and offers a broader range of application for the prosthesis according to the invention. A corresponding element is shown in FIG. 2d of the drawing and constitutes an alternative embodiment of shaft end 31 (here identified as 31'); in this embodiment, the roll faces 32 of an artificial knee joint are fixed to shaft end 31'.

The invention is not limited in its application to the above given example. Rather a plurality of variations are conceivable which utilize the illustrated solution even for principally different embodiments.

We claim:

1. In a resection prosthesis assembly unit comprising a head member and an end member of which one member is provided with a conical pin and the other member is provided with a conical bore and at least one intermediate member is provided which is adapted to the pin and/or the bore, with the different members, which abut when assembled, being secured against relative rotation by means of mutually adapted shaped portions, the improvement wherein: two of said members are constructed to be connected together by a pin-and-bore connection by insertion of a pin of one of the two members into a bore of the other of the two members in a selected insertion direction, said two members are provided with respective first surfaces which extend transversely to said insertion direction and which face one another and are spaced apart to define a recess when said two members are connected together so that said pin is fully inserted in said bore and said two members abut one another, one of said two members is further provided with a second surface extending in said insertion direction, and said recess is provided to receive a wedge insertable into said recess to bear against said first surfaces for forcing said two members apart while the forces exerted by the wedge are absorbed by said first surfaces and the wedge is guided by said second surface.

2. Assembly unit according to claim 1 for use with a wedge having a fork shape and the two tines of the fork each individually have a wedge shape, with two said recesses being provided at mutually facing external regions of the prosthesis parts and the space between the two fork tines being adapted to the distance between the two recesses.

3. Assembly unit according to claim 2, wherein said one of said two members is provided with two second surfaces constituting vertical external guide faces which correspond to the internal distance between correponding faces on the interior of the fork tines.

4. Assembly unit according to claim 1 wherein the longitudinal axis (13) of the intermediate member (5, 9) is curved similarly to the natural femur and the shaped portions (14, 15) of said two members are configured in such a manner that they fit into one another in two positions in which the abutting parts are rotated about their longitudinal axis (13) by an angle which is approximately 180° to the natural angle formed between the local planes of curvature of the longitudinal axes of the two natural, elongate portions of the thigh bones of a human being.

5. Assembly unit according to claim 4 wherein the shaped portions are configured to engage in one another with little play.

6. Assembly unit according to claim 4 wherein the shaped portions are formed as a lip and a recess on surfaces (16, 17) which face one another when the unit is assembled.

7. Assembly unit according to claim 6 wherein the shaped portions are designed as tongue (14) and groove (15).

8. Assembly unit according to claim 7 wherein the tongue (14') is curved at an obtuse angle and the groove (15') is widened in the form of a wedge at one of its ends.

9. Assembly unit according to claim 1 wherein the two members provided with a conical pin (11) and a conical bore (10), respectively, are designed in such a manner that, when assembled, said recess is located on the axis (13) of the cone.

10. Assembly unit according to claim 1 wherein the intermediate member (5) is provided with a longitudinal channel for an anchoring rod extending from the head member (1) to the end member (12).

11. Assembly unit according to claim 1 wherein said end member comprises a lower shaft element (31') provided with a connecting member or a roll surface (32), respectively, for an artificial knee joint.

* * * * *